United States Patent [19]
Mason et al.

[11] Patent Number: 5,962,728
[45] Date of Patent: Oct. 5, 1999

[54] ISOCYANATE RESIDUE PURIFICATION

[75] Inventors: Robert W. Mason; Farhad Fadakar; Joseph P. Bridges; Larry K. Butler; Majid Keyvani, all of Lake Charles, La.

[73] Assignee: Arco Chemical Technology, L.P., Greenville, Del.

[21] Appl. No.: 08/961,800

[22] Filed: Oct. 31, 1997

[51] Int. Cl.$^6$ .................... C07C 263/20; C07C 263/18
[52] U.S. Cl. ................................ 560/352; 210/770
[58] Field of Search ................ 560/352; 210/770

[56] References Cited

U.S. PATENT DOCUMENTS

| | | | |
|---|---|---|---|
| 3,317,959 | 5/1967 | List | 425/208 |
| 3,346,242 | 10/1967 | List | 366/81 |
| 3,347,528 | 10/1967 | List et al. | 366/75 |
| 3,480,997 | 12/1969 | List | 425/144 |
| 3,687,422 | 8/1972 | List | 366/289 |
| 3,689,035 | 9/1972 | List | 366/82 |
| 3,880,407 | 4/1975 | List | 366/99 |
| 4,216,063 | 8/1980 | Ailloud et al. | 203/91 |
| 4,412,073 | 10/1983 | Robin | 528/52 |
| 4,575,253 | 3/1986 | List et al. | 366/331 |
| 4,596,678 | 6/1986 | Merger et al. | 560/344 |
| 4,650,338 | 3/1987 | List et al. | 366/85 |
| 4,675,401 | 6/1987 | Robin | 544/193 |
| 4,748,226 | 5/1988 | Merger et al. | 528/85 |
| 4,774,357 | 9/1988 | Keggenhoff et al. | 560/352 |
| 4,871,460 | 10/1989 | Robin et al. | 210/634 |
| 4,871,828 | 10/1989 | Blind et al. | 528/44 |
| 4,918,220 | 4/1990 | Collas et al. | 560/352 |

*Primary Examiner*—Rabon Sergent
*Attorney, Agent, or Firm*—Dale Lynn Carlson; Wiggin & Dana

[57] ABSTRACT

The present invention relates to a process for isolating aliphatic isocyanate monomer(s) from a liquid or viscous paste composition comprising polymeric isocyanate residues and the aliphatic isocyanate monomer(s), and for isolating solid polymeric isocyanate residue from said composition. Also disclosed is the aliphatic isocyanate monomer(s) and the solid polymeric isocyanate byproduct produced by this process.

31 Claims, 2 Drawing Sheets

ISOCYANATE RESIDUE PURIFICATION

FIELD OF THE INVENTION

The present invention relates generally to a process for isolating isocyanate monomers, and more particularly to a process for isolating aliphatic isocyanate monomers from a crude residue mixture containing these monomers, and more specifically to a process that employs a dispersing evaporative dryer in combination with a heating step and a cooling step in order to recover isocyanate monomers and isolate an essentially monomer-free solid polymeric residue waste that may be easily disposed of.

BACKGROUND OF THE INVENTION

Isocyanates, such as toluene diisocyanate ("TDI") and their derivatives, such as thioisocyanates, are commercially important chemicals that are useful in the preparation of urethane foams, urethane elastomers, coatings, insecticides, herbicides, and the like. Isocyanates can be conveniently grouped into the broad categories of aromatic isocyanates and aliphatic isocyanates. Aromatic isocyanates, such as TDI, contain an aromatic group, such as a phenyl ring, in the molecular structure of the compound. Aliphatic isocyanates, on the other hand, include one or more aliphatic groups, such as butyl or cyclohexyl groups. Examples of this type of isocyanate include isophorone diisocyanate (IPDI), 1,6-diisocyanatohexane (HDI) and saturated 4,4'-diphenyl methane diisocyanate ($H_{12}MDI$).

Isocyanates are produced by a variety of commercially established procedures, such as phosgenation of primary amines, reaction of primary amines with carbon dioxide and acyl halide, and reaction of primary amines with carbon dioxide and hexamethyldisilazane. Unfortunately, during the manufacture of isocyanates using these procedures, an appreciable amount of monomeric isocyanate polymerizes to form a polymeric residue as a by-product. Thus, the total reaction product is a combination of desirable monomeric isocyanate molecules and undesirable polymerized isocyanate residue by-product. The polymerized isocyanate residue in the by-product is considered an impurity and reduces the overall yield of the synthesis reaction. In addition, since the by-product typically contains relatively low viscosity isocyanate monomer(s) that is difficult to separate from the polymerized isocyanate residue, the by-product itself is typically a viscous, sticky paste that interferes with processing and bulk transfer equipment. Moreover, since heretofore the isocyanate monomer(s) could not heretofore be easily separated from the by-product, an additional yield loss typically occurs due to these unrecovered monomers in the by-product.

There is a plethora of equipment available in the marketplace for effecting separations of compounds within mixtures, such as evaporators, extractors, and heated mixers. Heretofore, although effective separations have been carried out using aromatic isocyanate residues, the prior art methodology is generally not useful for making separations with respect to aliphatic isocyanate residues.

Illustrative of such separations, evaporative dryers such as wiped film evaporative ("WFE") dryers have been employed in the past in order to try to isolate aromatic isocyanate monomers (such as toluene diisocyanate monomers) from polymeric toluene diisocyanate residue. Falling film evaporative dryers, such as thin film evaporative ("TFE") dryers, have been employed to try to isolate aliphatic isocyanate monomers, such as IPDI monomers, HDI monomers and $H_{12}MDI$ monomers, from their respective polymeric residues. Unfortunately, these attempts have been less successful than might be desired since neither WFE nor TFE dryers enable the complete separation of isocyanate monomers from the polymeric residue. Indeed, the polymeric residue that is recovered from the WFE or TFE units typically contains approximately 30 to 50% by weight of monomeric isocyanate molecules based upon the weight of the residue. Thus, a significant amount of desirable monomer product typically remains unrecovered using these evaporative methods. Further, the unrecovered monomers cause residue to be in, or remain in, the form of a viscous paste that is difficult to remove from the evaporator. In order to remove this viscous paste from the WFE or TFE unit, the paste is typically solubilized in an organic solvent, such as chlorobenzene. Unfortunately, the residue containing such organic solvent is classified as toxic or hazardous waste, thus introducing a costly storage and/or disposal problem. As yet another alternative, the residue isolated from the WFE or TFE unit can be incinerated, but this alternative is costly and energy-intensive.

Another method of separating monomeric isocyanates from the solid polymeric residue is described in U.S. Pat. Nos. 4,871,828; 4,871,460; and 4,918,220 which disclose isolating isocyanate condensates using supercritical $CO_2$ extraction. Unfortunately, this method is also energy intensive, and requires specialized equipment.

As another alternative, U.S. Pat. No. 4,774,357 discloses purification of crude polyisocyanates by extraction in a two-phase system. However, large volumes of organic extractant are required in such a process, posing the aforementioned problem of disposal of hazardous or toxic waste.

Heated mixer-kneader-type dryers are known to be useful in carrying out thermal processes on liquid, pasty, and solid materials. U.S. Pat. No. 3,687,422 discloses a multiple spindle mixing kneader that includes paddles, disc sectors, and kneading bars as product manipulation means. These elements are arranged so that the processed material is wiped on the heated inner surface of the housing to provide a large surface from which vaporization of volatile materials may take place. Other heated mixer-kneader dryers are disclosed in U.S. Pat. Nos. 3,317,959; 3,346,242; 3,347,528; 3,480,997; 3,689,035; 3,880,407; 4,575,253; and 4,650,338. U.S. Pat. No. 4,216,063 issued to Ailloud et al. discloses a method of continuously purifying toluene diisocyanate (TDI) to high purity using an agitated, scraped evaporator in combination with increasing evaporation temperature from within the range of about 70° C. to 175° C. up to a temperature within the range of about 210° C. to 250° C., using a pressure within the range of 1–50 mm Hg. The isolated residue product is said to be a dry, friable solid that is easily collected and disposed of. The process disclosed in the '063 patent, however, is limited to purification of one aromatic isocyanate, TDI, under the processing conditions described hereinabove. Attempts by the present inventors to adopt the process disclosed in the '063 patent for use on aliphatic isocyanates have been unsuccessful, resulting in a sticky, viscous paste that clogs the processing equipment, and is difficult to collect and dispose of.

In view of the above, it is clear that there is a need in the isocyanates manufacturing community for improved processes for isolating aliphatic isocyanate monomers from polymeric residue byproducts while simultaneously providing a waste residue that is easily handled and disposed of. The present invention provides one answer to that need.

SUMMARY OF THE INVENTION

In one aspect, the present invention relates to a process for isolating aliphatic isocyanate monomer(s) from a liquid or viscous paste composition comprising polymeric isocyanate residues and the aliphatic isocyanate monomer(s), and for isolating solid polymeric isocyanate residue from said composition, said process comprising the steps of:

(a) introducing said composition into a heating zone of a dispersing evaporative dryer comprising said heating zone and a cooling zone;

(b) heating said composition in said heating zone to an elevated temperature sufficient to cause at least a portion of said aliphatic isocyanate monomer(s) in said composition to evaporate, thus forming a gaseous stream of aliphatic isocyanate monomer(s) and a molten stream of polymeric residue byproduct that is substantially free of aliphatic isocyanate monomer(s);

(c) moving said molten stream from said heating zone to said cooling zone of said dispersing evaporative dryer, and cooling said molten stream to cause said molten stream to solidify, thus forming said solid polymeric isocyanate residue. Preferably, this process additionally comprises the step of separating the gaseous stream from said solid polymeric isocyanate residue.

In another aspect, the present invention relates to a process for isolating aliphatic diisocyanate monomers and forming a solid residue from a crude residue mixture containing the aliphatic diisocyanate monomers, said process comprising the steps of:

(a) introducing said crude residue mixture containing aliphatic diisocyanate monomers selected from the group consisting of isophorone diisocyanate (IPDI), 1,6-diisocyanatohexane (HDI), saturated 4,4'-diphenyl methane diisocyanate ($H_{12}$MDI), and combinations thereof into a heating zone of a dispersing evaporative dryer;

(b) heating said crude residue mixture to cause at least a portion of said aliphatic diisocyanate monomers in said crude residue mixture to evaporate, thus forming a gaseous stream of aliphatic diisocyanate monomers and a molten stream of substantially aliphatic diisocyanate monomer-free residue;

(c) moving said molten stream of substantially aliphatic diisocyanate monomer-free residue from said heating zone to a cooling zone of said dispersing evaporative dryer, and cooling said molten stream to solidify as a dry solid residue.

In another aspect, the present invention relates to a process for isolating aliphatic isocyanate monomers and forming a solid residue from a crude residue mixture containing the aliphatic isocyanate monomers, said process comprising the steps of (a) introducing said crude residue mixture into a thermal evaporative dryer selected from the group consisting of a wiped film evaporative dryer and a thin film evaporative dryer, said thermal evaporative dryer evaporating a first portion of said isocyanate monomers to form a first gaseous stream of isocyanate monomers and a molten stream of crude residue comprising a second portion of said isocyanate monomers;

(b) introducing said molten stream of crude residue into the heating zone of a dispersing evaporative dryer;

(c) heating said molten stream of crude residue to cause at least a portion of said second portion of said isocyanate monomers to evaporate from said crude residue thus forming a second gaseous stream of isocyanate monomers and a molten stream of substantially isocyanate monomer-free residue; and (d) moving said molten stream of substantially isocyanate monomer-free residue from said heating zone to a cooling zone of said dispersing evaporative dryer, and cooling said molten stream to cause said molten stream to solidify as a solid residue.

In yet another aspect, the present invention relates to a process for isolating diisocyanate monomers and forming a solid residue from a crude residue mixture containing the diisocyanate monomers, said process comprising the steps of:

(a) introducing said crude residue mixture containing diisocyanate monomers selected from the group consisting of toluene diisocyanate (TDI), isophorone diisocyanate (IPDI), 1,6-diisocyanatohexane (HDI), saturated 4,4'-diphenyl methane diisocyanate ($H_{12}$MDI), and combinations thereof into a thermal evaporative dryer selected from the group consisting of a wiped film evaporative dryer and a thin film evaporative dryer, said thermal evaporative dryer evaporating a first portion of said diisocyanate monomers to form a first gaseous stream of diisocyanate monomers and a molten stream of crude residue comprising a second portion of said diisocyanate monomers;

(b) introducing said molten stream of crude residue into the heating zone of a dispersing evaporative dryer;

(c) heating said molten stream to cause at least a portion of said second portion of said diisocyanate monomers to evaporate from said crude residue, thus forming a second gaseous stream of diisocyanate monomers and a molten stream of substantially diisocyanate monomer-free residue; and (d) moving said molten stream of substantially diisocyanate monomer-free residue from said heating zone to a cooling zone of said dispersing evaporative dryer, and cooling said molten stream of substantially diisocyanate monomer-free residue to cause said molten stream to solidify as a solid residue.

In yet another aspect, the present invention relates to the liquid isocyanate monomers and the solid polymeric isocyanate residue produced by the above processes.

These and other aspects will become apparent upon reading the following detailed description of the invention.

BRIEF DESCRIPTION OF THE DRAWINGS

The invention will be more fully understood from the following detailed description taken in conjunction with the accompanying drawings in which.

DETAILED DESCRIPTION OF THE INVENTION

Figure 1:
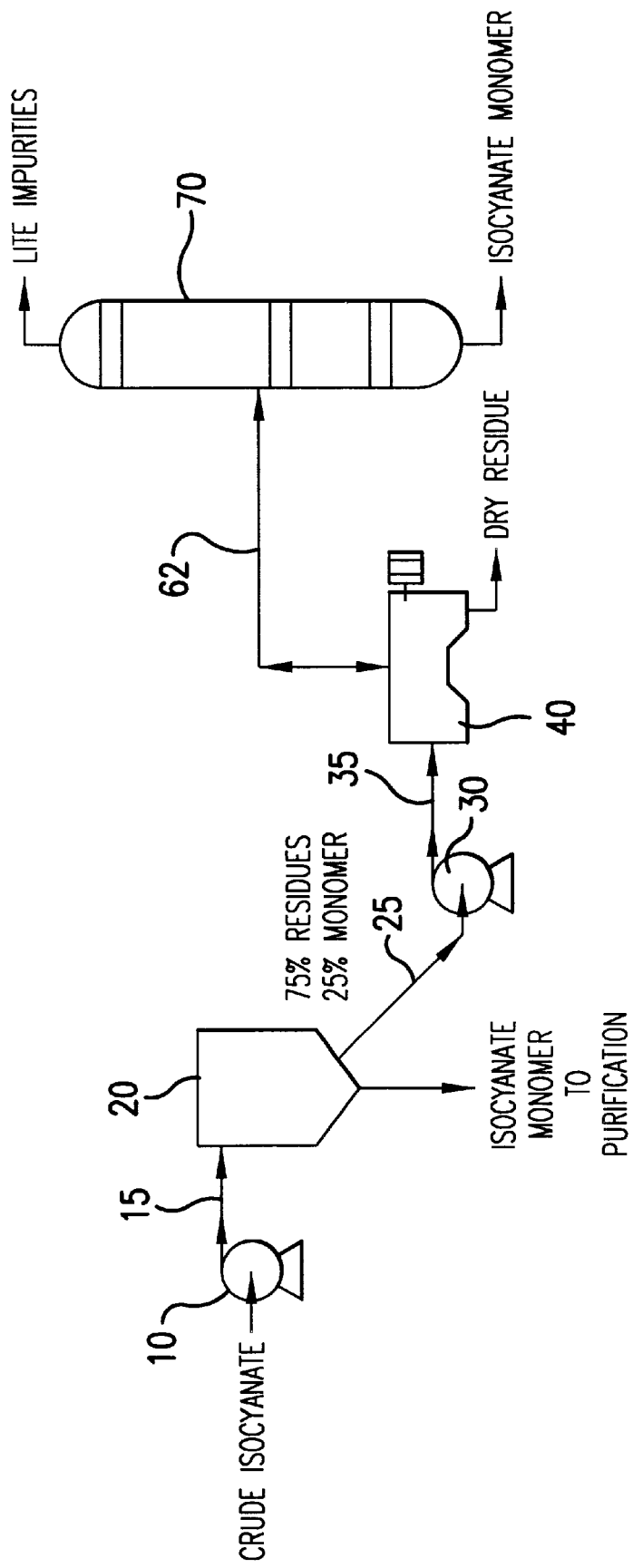
FIG. 1 is a schematic diagram of the process of the invention.

It now has been surprisingly found, in accordance with the present invention, that a solution is provided to the difficulty associated with isolating aliphatic isocyanate monomers from polymeric isocyanate residues in order to provide a high yield of desirable monomers while generating a waste product that is easily handled and disposed of. More specifically, in contrast to prior art methodology which produces a viscous paste or fluid glass form of polymeric isocyanate by-product and which leaves significant amounts of monomeric isocyanate unrecovered, the present invention employs a cooling zone in conjunction with a dispersing evaporative dryer to cause the polymeric aliphatic isocyanate residue to solidify, thus making it easy to collect and dispose of. Thus, the present invention minimizes the formation of solid polymeric residue and maximizes the recovery of the desirable monomeric isocyanates.

The solidified polymeric isocyanate residue byproduct produced in the process of the present invention has a monomer content of less than 1%, preferably less than 0.1%. The recovery of aliphatic isocyanate monomer using the purification methods of the invention are in excess of 99% of total monomer in the monomer/polymer mixture.

As used herein, the term "isocyanate" refers to compounds having at least one isocyanate (NCO) group, and is intended to encompass derivatives such as thioisocyanates. The term "aliphatic isocyanate" refers to any aliphatic (or cycloaliphatic) compound containing at least one isocyanate group. The term "dispersing evaporative dryer" refers to those evaporative dryers which mechanically distribute at least a portion of the material being dried over a surface within the drier.

The chemistry of isocyanate production is well known. In general terms, isocyanates that are purified by the process of the invention may be produced by any method known in the art, such as phosgenation of primary amines. In the phosgenation reaction, phosgene ($COCl_2$) is reacted with an amine or diamine compound in an organic solvent such as monochlorobenzene or dichlorobenzene. If diisocyanate monomers are desired, an aliphatic diamine, such as hexane diamine, isophorone diamine, or saturated 4,4'-diphenyl methane diamine is used in the reaction. Reaction conditions vary according to specific product objectives and are well known to those skilled in the art. Exemplary pressures and temperatures for the phosgenation reaction are in the range of from 0 to 2000 psi and 0 to 200° C., respectively. Contaminants and by-products in the reaction product include hydrochloric acid (HCl), unreacted phosgene, solvent, and polymerized isocyanate residue. These contaminants and by-products are removed in subsequent purification steps outlined below.

Purification of the aliphatic isocyanate monomers is performed in several stages. Generally, unreacted phosgene and HCl are removed using a phosgene stripper column, while excess solvent is removed by conventional distillation under vacuum. Both of these processes are known in the art. The undistillable portion of the remaining product is generally a crude mixture of monomeric aliphatic isocyanate and high molecular weight, polymerized isocyanate. In order to increase the yield of aliphatic isocyanate monomer, the crude mixture is subjected to further purification steps described in FIG. 1.

Referring now to FIG. 1, the crude mixture is transported by pump 10 through line 15 into a primary evaporative dryer 20. The primary evaporative dryer 20 is preferably either a wiped film evaporative dryer (WFE) or a thin film evaporative dryer (TFE), both of which are commercially available.

When employing a wiped film evaporative dryer, or WFE, in the process of the present invention, at least a portion of the crude mixture of monomeric isocyanate and polymerized isocyanate typically resulting from isocyanate production processes, is pressed or "wiped" onto the walls of the evaporative dryer that are maintained at an elevated temperature. The heat from the walls causes the aliphatic isocyanate monomer to vaporize, while the high molecular weight, polymerized isocyanate residue continues to be "wiped" down the walls of the evaporative dryer. The vaporized aliphatic isocyanate monomers are recovered by condensation. At this stage, the concentrated polymerized aliphatic isocyanate residue takes the form of a viscous paste or glass.

When employing a thin film evaporative dryer (or TFE, also known as a falling film evaporative dryer), at least a portion of the crude mixture of monomeric isocyanate and polymerized isocyanate typically resulting from isocyanate production processes, is deposited onto a vertically-oriented surface maintained at an elevated temperature. The crude mixture is pulled down the heated surface by gravity, thus causing the monomeric aliphatic isocyanates to vaporize. The vaporized monomeric aliphatic isocyanates are recovered by conventional condensation. At this stage of purification, the concentrated polymerized isocyanate residue takes the form of a viscous paste or glass.

Both the WFE and TFE purification methods result in a mixture of aliphatic isocyanate polymers that contain about 20–50% by weight of desirable monomers. Thus, a significant amount of desirable aliphatic monomer product remains in the crude product even after purification in the primary evaporative dryer. However, it has been surprisingly found that addition of a dispersing evaporative dryer, such as a List evaporative dryer as a secondary purification device, followed by the use of the residue solids cooling device, improves recovery of aliphatic isocyanate monomer, and results in a total recovery of available aliphatic isocyanate monomer in excess of 99% of total monomer in the monomer/polymer mixture.

Referring again to FIG. 1, the partially purified residue material emerging from the primary evaporative dryer 20 (which contains approximately 25% by weight monomeric aliphatic isocyanate product) is transported by pump 30 through lines 25 and 35 into a dispersing evaporative dryer 40. Dispersing evaporative dryers are generally known in the field of high viscosity processing technology. Particularly useful units are available from List AG, Arisdorf, Switzerland and are described in U.S. Pat. Nos. 3,317,959; 3,346,242; 3,347,528; 3,480,997; 3,689,035; 3,880,407; 4,575,253; and 4,650,338, each of which is incorporated by reference herein.

As mentioned above, dispersing evaporative dryers have been described for use in recovery of TDI, an aromatic diisocyanate. Briefly, the evaporative dryer used in recovery of TDI was the "AP (All-Phase) CONTI" unit, a high volume, continuously operating turnshaft mixing and kneading reactor for thermal processes involving highly viscous, pasty products or solids that pass through a sticky, crust-forming phase during processing. However, this particular unit maintains a single temperature throughout the processing area, and specific areas of the device cannot be cooled.

A preferred dispersing evaporative dryer 40 for use in the present invention is a mixing/kneading evaporative dryer such as the DISCOTHERM B unit sold commercially by List AG, Arisdorf, Switzerland. This device is useful in processing viscous, pasty, or crusting materials, such as the residue resulting from the WFE or TFE evaporative dryer. Generally, the unit comprises a horizontal housing in which a shaft carrying a number of disc elements rotates. Housing, shaft, and disc elements, all of which contribute to thermal transfer, can be heated or cooled separately. The unit results in intensive dispersing of the polymeric isocyanate material onto the walls of the evaporative dryer. This results in optimal conditions for heat and vapor transfer which is critical when processing a crude mixture of monomeric aliphatic isocyanate and high molecular weight, polymerized isocyanate. Advantageously, the unit incorporates separate heating or cooling zones which facilitate efficient thermal control of aliphatic isocyanate recovery.

Figure 2:
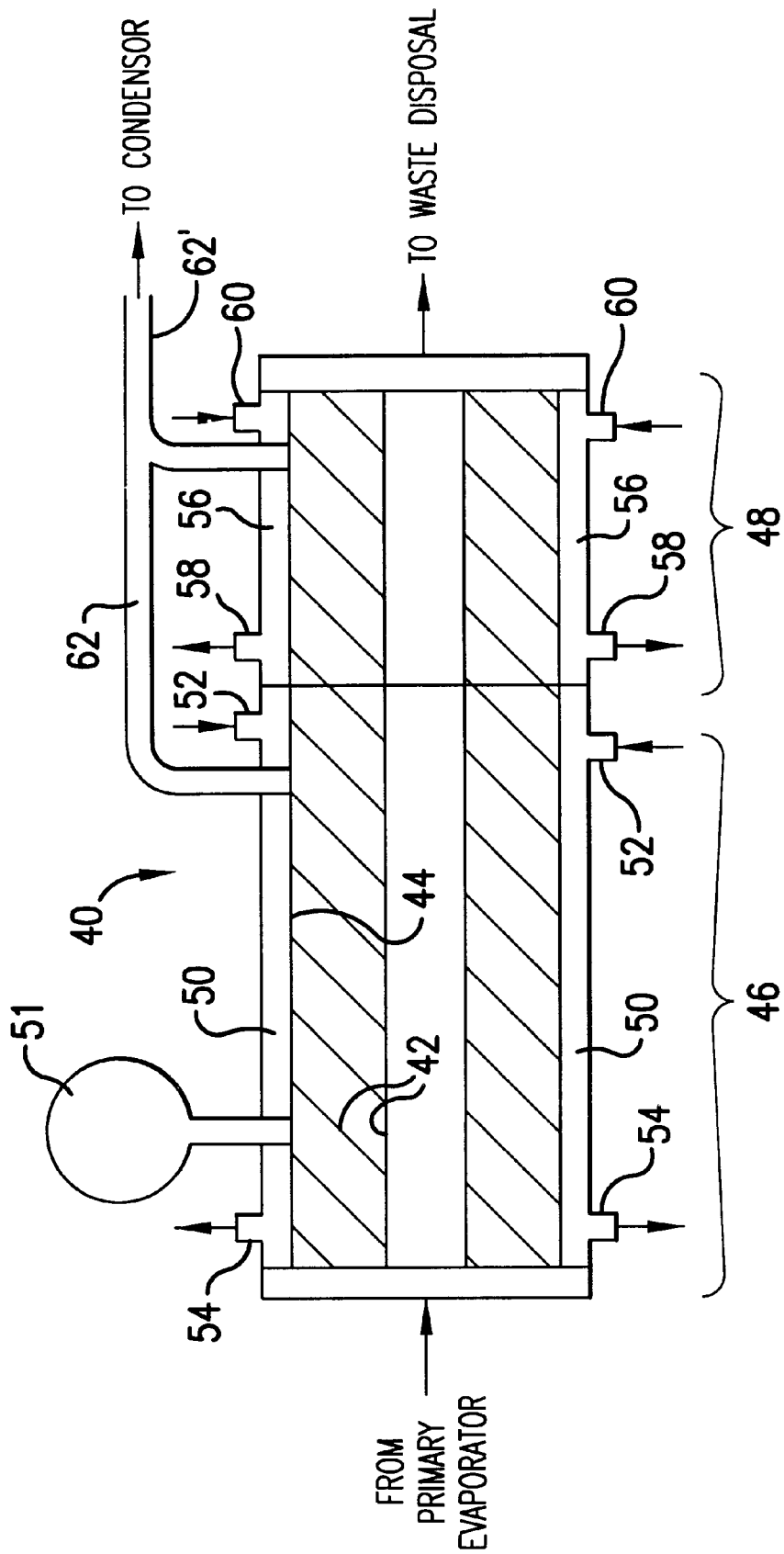
FIG. 2 is a schematic diagram of a dispersing evaporative dryer useful in the method of the invention.

A schematic diagram of a commercially available evaporative dryer with separate heating and cooling zones is shown in FIG. 2 at 40. The unit consists of an axially mounted rotor and screw blade assembly 42. The rotor and screw blade assembly 42 is positioned in a housing 44 and driven by motor 41. The unit 40 is divided into a heating zone 46 and a cooling zone 48, and the temperature of each is controlled separately. The walls of the heating zone 46 are maintained at temperatures at or above the vaporization temperature of the aliphatic isocyanate monomer. Generally, the temperature of the walls of the housing in the heating zone 46 ranges from about 250° C. to about 280° C., and is maintained by heated oil that is recirculated through a jacket 50. As shown in FIG. 2, heated oil is fed into the jacket 50 by inlet pipes 52 and returned by outlet pipes 54.

A cooling step is a unique feature in the method of the invention, and is important in efficiently isolating aliphatic isocyanates and granular friable polymeric waste. As shown in FIG. 2, material leaving the heating zone 46 is transported continuously to the cooling zone 48 by the rotor and screw assembly 42. The walls of the cooling zone are preferably maintained at a temperature at which the polymerized aliphatic isocyanate residue forms a friable solid that is easily collected and disposed. The temperature of the walls of the cooling zone 48 preferably ranges from about 100° C. to about 120° C., and is maintained by heated water, steam, or oil that is recirculated through a jacket 56. As shown in FIG. 2, heated water, steam, or oil is fed into the jacket 56 by inlet pipes 60 and returned by outlet pipes 58.

During operation, aliphatic isocyanate residue from the primary evaporative dryer 20 enters the heating zone 46 of the dispersing evaporative dryer 40 and is manipulated by the rotor and screw blade assembly 42. Preferably, the dispersing evaporative dryer is evacuated (e.g., to approximately 1–5 mm Hg) by vacuum pump 51 to facilitate removal of aliphatic isocyanate monomer. During manipulation, the screw blades disperse the aliphatic isocyanate residue such that the entire volume of residue is repeatedly exposed to the heated inner walls of the heating zone. During this exposure, remaining aliphatic isocyanate monomer that was not recovered in the primary evaporative dryer 20 is vaporized in the dispersing evaporative dryer 40 and transferred through collection pipe 62 to condenser 70. The vaporized aliphatic isocyanate monomer is condensed in a condenser 70 and recovered for use. Light impurities not recovered in the condenser 70 are incinerated. The remaining hot polymerized isocyanate residue takes the form of a fluid glass and is difficult to handle and dispose. This material is transferred to the cooling zone 48 for further processing.

As the screw and blade assembly 42 continues to rotate, the heated polymerized isocyanate residue is continuously transferred to the cooling zone 48 of the dispersing evaporative dryer 40. The heated polymerized isocyanate residue enters the cooling zone 48 as a fluid glass and is cooled as it comes in contact with the cooler walls of the cooling zone. In the cooling zone, the polymeric isocyanate residue in the fluid glass state is transformed to a solid which is continuously broken up by the blades of the screw blade assembly 42 into a friable, granular solid that is easily collected and disposed. Like the heating zone 46, the cooling zone 48 is evacuated to approximately 1–50 mm Hg. Thus, any remaining vaporized aliphatic isocyanate monomer is collected through collection pipe 62' and transferred to the condenser 70.

After purification, the polymerized isocyanate residue that emerges from the cooling zone 48 has an aliphatic isocyanate monomer content of less than 1% and preferably less than 0.1%. The resulting total recovery of available aliphatic isocyanate monomer using the purification methods of the invention are in the range of 95–98%.

The following examples illustrate, but are not intended to limit the scope of, the present invention. All parts and percentages are by weight and all temperature are by degrees Celsius, and all molecular weights are number average molecular weights, unless explicitly stated otherwise.

EXAMPLE 1

Purification of Saturated 4,4'-Diphenyl Methane Diisocyanate

Saturated 4,4'-diphenyl methane diisocyanate ($H_{12}$MDI) was synthesized using saturated 4,4'-diphenyl methane diamine ($H_{12}$MDA) and phosgene ($COCl_2$) in chlorobenzene as described above. The crude reaction product was a combination of $H_{12}$MDI monomers, polymerized $H_{12}$MDI, HCl, phosgene, and solvent. Unreacted phosgene and HCl were removed using a phosgene stripper column, and excess solvent was removed by conventional distillation under vacuum. The remaining crude mixture of $H_{12}$MDI monomers and polymerized $H_{12}$MDI was passed through a TFE unit at approximately 180° C. and 1–2 mm Hg to collect a portion of the $H_{12}$MDI monomers. This portion of monomers is isolated by condensation. At this point, the residue consisted of approximately 50% monomer and 50% polymeric oligomers and was subjected to further processing in a dispersing evaporative dryer.

Approximately 6.8 kg of $H_{12}$MDI residue was fed into a dispersing evaporative dryer (a List DISCOTHERM B evaporative dryer, List AG, Switzerland) having a heating zone and a cooling zone. The heating zone was held at 250–280° C. by hot circulating oil and about 5 mm Hg. The rotor and screw blade assembly was set to rotate at about 30 rpm. After approximately 45 minutes in the heating zone, the material was transferred to the cooling zone held at approximately 100° C. and 5 mm Hg. The residue was processed in the cooling zone for approximately 10 minutes, and the collected $H_{12}$MDI vapor was collected and condensed. The residue extruded from the dispersing evaporative dryer was a dry friable polymer residue containing less than 100 ppm (<0.01%) monomeric $H_{12}$MDI as evaluated by gas chromatography.

EXAMPLE 2

Purification of Isophorone Diisocyanate

Isophorone diisocyanate (IPDI) was synthesized using isophorone diamine (IPDA) and phosgene ($COCl_2$) in chlorobenzene as described above. The purification procedures and conditions were the same as outline in Example 1. The residue extruded from the dispersing evaporative dryer was a dry friable polymer residue containing less than 1% monomeric IPDI.

EXAMPLE 3

Purification of 1,6-Diisocyanatohexane 1,6-diisocyanatohexane (HDI) was synthesized using hexamethylenediamine (HMD) and phosgene ($COCl_2$) in chlorobenzene as described above. The purification procedures and conditions were the same as outline in Example 1. The residue extruded from the dispersing evaporative dryer was a dry friable polymer residue containing less than 0.1% monomeric HDI.

EXAMPLES 4–11

Purification of Isophorone Diisocyanate

Examples 4–11 are summarized in Table 1. In all of these examples, IPDI was prepared as described above. Approximately 400 kg of the crude reaction product was purified in a TFE unit. Various amounts of the material discharged from the TFE unit were further purified in a List DISCOTHERM B dispersing evaporative dryer as described above and under conditions described in Table 1.

TABLE 1

| Example | Charge (Kg) | Jacket Temp (° C.) | Pressure (mm Hg) | Screw Speed (rpm) | Batch Time (h) | Mass Balance Recovery (%) |
|---|---|---|---|---|---|---|
| 4  | 9.5  | 258 | 0.43–22  | 31 | 5.3  | ND    |
| 5  | 6.8  | 258 | 6.7      | 30 | 0.8  | 93.07 |
| 6  | 4.52 | 257 | 6.7–13.6 | 44 | 0.72 | 83.0  |
| 7  | 6.8  | 239 | 0        | 29 | 1.07 | 94.27 |
| 8  | 6.8  | 284 | 6.7–13.6 | 30 | 0.45 | 99.93 |
| 9  | 6.8  | 257 | 6.7–13.6 | 44 | 0.58 | 99.13 |
| 10 | 6.8  | 247 | 6.7–21   | 42 | 0.90 | 97.8  |
| 11 | 6.8  | 247 | 6.7–27   | 42 | 0.85 | 95.13 |

In all cases the cooling stage cooled the processed residue mixture to approximately 80–100° C. after which it formed a friable, granular solid. Recovery of the monomeric IPDI from the monomer/residue mixture was approximately 85–90% in all cases.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entirety.

What is claimed is:

1. A process for isolating aliphatic isocyanate monomer(s) from a liquid or viscous paste composition comprising polymeric isocyanate residues and the aliphatic isocyanate monomer(s), and for isolating solid polymeric isocyanate residue from said composition, said process comprising the steps of:
   (a) introducing said composition into a heating zone of a dispersing evaporative dryer comprising said heating zone and a cooling zone;
   (b) heating said composition in said heating zone to an elevated temperature sufficient to cause at least a portion of said aliphatic isocyanate monomer(s) in said composition to evaporate, thus forming a gaseous stream of aliphatic isocyanate monomer(s) and a molten stream of polymeric residue byproduct;
   (c) moving said molten stream from said heating zone to said cooling zone of said dispersing evaporative dryer, and cooling said molten stream to cause said molten stream to solidify, thus forming said solid polymeric isocyanate residue having an isocyanate monomer content of less than 1% by weight.

2. The process of claim 1 which additionally comprises the step of separating said gaseous stream from said solid polymeric isocyanate residue.

3. The process of claim 1 wherein said heating zone of said dispersing evaporative dryer is maintained at a temperature between about 250° C. and about 280° C.

4. The process of claim 1 wherein said cooling zone of said dispersing evaporative dryer is maintained at a temperature between about 100° C. and about 120° C.

5. The process of claim 1 wherein said heating zone and said cooling zone are separately maintained at a pressure between about 1 and about 5 mm Hg.

6. The process of claim 1 wherein said aliphatic isocyanate monomer(s) is selected from the group consisting of aliphatic monoisocyanate monomers, aliphatic diisocyanate monomers, aliphatic triisocyanate monomers, and combinations thereof.

7. The process of claim 1 wherein said aliphatic isocyanate monomer(s) is selected from the group consisting of isophorone diisocyanate (IPDI), 1,6-diisocyanatohexane (HDI), saturated 4,4'-diphenyl methane diisocyanate ($H_{12}$MDI), and combinations thereof.

8. The process of claim 1 wherein said dispersing evaporative dryer is a mixing/kneading evaporative dryer.

9. The process of claim 1 which further comprises collecting said solid polymeric isocyanate residue, and condensing said gaseous stream of isocyanate monomer(s) to form liquid isocyanate monomer(s).

10. The process of claim 1 wherein the solid polymeric isocyanate residue has an isocyanate monomer content of less than 0.1% by weight.

11. A process for isolating aliphatic diisocyanate monomers and forming a polymeric isocyanate solid residue from a crude residue mixture containing the aliphatic diisocyanate monomers, said process comprising the steps of:
   (a) introducing said crude residue mixture containing aliphatic diisocyanate monomers selected from the group consisting of isophorone diisocyanate (IPDI), 1,6-diisocyanatohexane (HDI), saturated 4,40-diphenyl methane diisocyanate ($H_{12}$MDI), and combinations thereof into a heating zone of a dispersing evaporative dryer;
   (b) heating said crude residue mixture to cause at least a portion of said aliphatic diisocyanate monomers in said crude residue mixture to evaporate, thus forming a gaseous stream of aliphatic diisocyanate monomers and a molten stream of polymeric isocyanate residue; and
   (c) moving said molten stream of substantially aliphatic diisocyanate monomer-free residue from said heating zone to a cooling zone of said dispersing evaporative dryer, and cooling said molten stream to solidify said polymeric isocyanate residue as a dry solid residue having an isocyanate monomer content of less than 1% by weight.

12. The process of claim 11 which additionally comprises the step of separating said gaseous stream from said solid residue.

13. The process of claim 11 wherein said heating zone of said dispersing evaporative dryer is maintained at a temperature between about 250° C. and about 280° C., and said cooling zone of said dispersing evaporative dryer is maintained at a temperature between about 100° C. and about 120° C.

14. The process of claim 11 wherein said heating zone and said cooling zone are separately maintained at a pressure between about 1 and about 5 mm Hg.

15. The process of claim 11 further comprising the step of collecting said gaseous stream.

16. The process of claim 11 further comprising the step of collecting said solid residue.

17. The process of claim 11 wherein the dry solid residue has an isocyanate monomer content of less than 0.1% by weight.

18. A process for isolating aliphatic isocyanate monomers and forming a solid residue from a crude residue mixture containing the aliphatic isocyanate monomers, said process comprising the steps of:

(a) introducing said crude residue mixture into a thermal evaporative dryer selected from the group consisting of a wiped film evaporative dryer and a thin film evaporative dryer, said thermal evaporative dryer evaporating a first portion of said isocyanate monomers to form a first gaseous stream of isocyanate monomers and a molten stream of crude residue comprising a second portion of said isocyanate monomers;

(b) introducing said molten stream of crude residue into the heating zone of a dispersing evaporative dryer;

(c) heating said molten stream of crude residue to cause at least a portion of said second portion of said isocyanate monomers to evaporate from said crude residue thus forming a second gaseous stream of isocyanate monomers and a molten stream of polymeric isocyanate residue; and (d) moving said molten stream of polymeric isocyanate residue from said heating zone to a cooling zone of said dispersing evaporative dryer, and cooling said molten stream to cause said molten stream to solidify as a solid polymeric isocyanate residue having an isocyanate monomer content of less than 1% by weight.

19. The process of claim 18 which comprises the additional step of separating said second gaseous stream from said solid residue.

20. The process of claim 18 wherein said heating zone of said dispersing evaporative dryer is maintained at a temperature between about 250° C. and about 280° C.

21. The process of claim 18 wherein said cooling zone of said dispersing evaporative dryer is maintained at a temperature between about 100° C. and about 120° C.

22. The process of claim 18 wherein said heating zone and said cooling zone are separately maintained at a pressure between about 1 and about 5 mm Hg.

23. The process of claim 18 wherein said isocyanate monomers are selected from the group consisting of monoisocyanate monomers, diisocyanate monomers, triisocyanate monomers, and combinations thereof.

24. The process of claim 18 wherein said isocyanate monomers are selected from the group consisting of isophorone diisocyanate (IPDI), 1,6-diisocyanatohexane (HDI), saturated 4,4'-diphenyl methane diisocyanate (H12MDI), and combinations thereof.

25. The process of claim 18 further comprising the step of collecting and combining said first and second gaseous streams.

26. The process of claim 18 further comprising the step of collecting said solid residue.

27. The process of claim 18 wherein the dry solid residue has an isocyanate monomer content of less than 0.1% by weight.

28. A process for isolating diisocyanate monomers and forming a solid residue from a crude residue mixture containing the diisocyanate monomers, said process comprising the steps of:

(a) introducing said crude residue mixture containing diisocyanate monomers selected from the group consisting of toluene diisocyanate (TDI), isophorone diisocyanate (IPDI), 1,6-diisocyanatohexane (HDI), saturated 4,4'-diphenyl methane diisocyanate (H12MDI), and combinations thereof into a thermal evaporative dryer selected from the group consisting of a wiped film evaporative dryer and a thin film evaporative dryer, said thermal evaporative dryer evaporating a first portion of said diisocyanate monomers to form a first gaseous stream of diisocyanate monomers and a molten stream of crude residue comprising a second portion of said diisocyanate monomers;

(b) introducing said molten stream of crude residue into the heating zone of a dispersing evaporative dryer;

(c) heating said molten stream to cause at least a portion of said second portion of said diisocyanate monomers to evaporate from said crude residue, thus forming a second gaseous stream of diisocyanate monomers and a molten stream of polymeric isocyanate residue; and (d) moving said molten stream of polymeric isocyanate residue from said heating zone to a cooling zone of said dispersing evaporative dryer, and cooling said molten stream of polymeric isocyanate residue to cause said molten stream to solidify as a solid residue having an isocyanate monomer content of less than 1% by weight.

29. The process of claim 28 which comprises the additional step of separating said second gaseous stream from said solid residue.

30. The process of claim 28 wherein said heating zone of said dispersing evaporative dryer is maintained at a temperature between about 250° C. and about 280° C., and said cooling zone of said dispersing evaporative dryer is maintained at a temperature between about 100° C. and about 120° C.

31. The process of claim 28 wherein said heating zone and said cooling zone are separately maintained at a pressure between about 1 and about 5 mm Hg.

* * * * *